(12) United States Patent
Dro (10) Patent No.: US 8,784,494 B2
(45) Date of Patent: Jul. 22, 2014

(54) SHOULDER IMPLANT METHOD (76) Inventor: Daniel William Dro, Carmel, IN (US)

(*) Notice: Subject to any disclaimer, the term of this patent is extended or adjusted under 35 U.S.C. 154(b) by 0 days.

(21) Appl. No.: 13/487,783

(22) Filed: Jun. 4, 2012

(65) Prior Publication Data
US 2012/0310359 A1 Dec. 6, 2012

Related U.S. Application Data (60) Provisional application No. 61/492,986, filed on Jun. 3, 2011.

(51) Int. Cl.
A61F 2/40 (2006.01)

(52) U.S. Cl.
USPC .................. 623/19.11; 623/19.12; 623/19.13

(58) Field of Classification Search
USPC ........................................... 623/19.11–19.14
See application file for complete search history.

(56) References Cited

U.S. PATENT DOCUMENTS

| 6,530,957 | B1* | 3/2003 | Jack | 623/19.14 |
| 6,986,790 | B2* | 1/2006 | Ball et al. | 623/19.11 |
| 2001/0049561 | A1* | 12/2001 | Dews et al. | 623/19.14 |
| 2009/0118837 | A1* | 5/2009 | Winslow et al. | 623/19.14 |

OTHER PUBLICATIONS

Clinton, J. et al.; Shoulder Hemiarthroplasty With Nonprosthetic Glenoid Arthroplasty: The Ream and Run; Techniques in Shoulder & Elbow Surgery; 10(1), Mar. 2009; p. 43-52.*
Biomet Product Brochure: Bio-Modular®/Bi-Polar Shoulder Arthroplasty: 1997.*
Worland et al., "Bipolar shoulder arthroplasty for rotator cuff arthropathy", Journal of Shoulder and Elbow Surgery, 1997;6, 512-515.*

* cited by examiner

Primary Examiner — David Isabella
Assistant Examiner — Dinah Baria
(74) Attorney, Agent, or Firm — Frost Brown Todd LLC (57) ABSTRACT An apparatus has a head, a neck, and a stem. The head is shaped to be insertable into an interval. The interval is formed using a reamed upper glenoid, a coracoid, and an acromion. The neck is in communication with the head. The neck is dimensioned to seat the head in the interval formed by the reamed upper glenoid, the coracoid, and the acromion. The stem is in communication with the neck. The stem is shaped to be insertable into a humerus.

10 Claims, 9 Drawing Sheets

SHOULDER IMPLANT METHOD

PRIORITY

This application claims priority to U.S. Provisional Patent Application Ser. No. 61/492,986, filed Jun. 3, 2011, entitled "SHOULDER IMPLANT DEVICE AND METHOD," the disclosure of which is incorporated by reference herein.

FIELD

Embodiments of the present invention relate, in general, to a shoulder implant device for use with an associated shoulder replacement method.

BACKGROUND

Rotator cuff arthropathy is a disabling condition caused typically by a long standing substantial tear of the rotator cuff. One effect of such a tear is that it may result in changing the mechanics of the shoulder unfavorably. Additionally, the shoulder may become arthritic and painful contributing to extreme discomfort for a patient.

Treatment of rotator cuff arthropathy has produced many challenges in reconstruction. Prior art includes shoulder joint replacement, reverse shoulder replacement, oversized head implants, and Cufftear Arthropathy (CTA) head by DePuy®. Each may overcome some of the pain and/or lack of function that results from rotator cuff arthropathy, but each also has shortcomings depending on the conditions of the reconstruction and the long term requirements of the reconstruction. For example, the CTA head by Depuy® may provide relief from pain and improvement of function if the patient has a sufficiently intact subscapularis muscle-tendon unit. Otherwise, it may prove unstable and therefore fail to improve function.

If inserted properly, the reverse shoulder replacement can, in the short-term, improve function and relief from pain even when the subscapularis muscle-tendon unit is insufficient. However it has a high mid-term and long-term failure rate due to loosening and dislocation, necessitating further surgery. This problem may arise because the gross alteration of shoulder anatomy demanded by the reverse shoulder prosthesis.

It would seem therefore, that a more successful treatment of rotator cuff arthropathy is desired.

BRIEF DESCRIPTION OF THE DRAWINGS

The accompanying drawings incorporated in and forming a part of the specification illustrate several aspects of the present disclosure, and together with the description serve to explain the principles of the invention; it being understood, however, that the described embodiments are not limited to the precise arrangements shown. In the drawings, like reference numerals refer to like elements in the several views. In the drawings.

DETAILED DESCRIPTION

The following description of certain examples should not be used to limit the scope of the present invention. Other features, aspects, and advantages of the embodiments disclosed herein will become apparent to those skilled in the art from the following description, which is by way of illustration, one of the best modes contemplated for carrying out the invention. As will be realized, the embodiments described herein are capable of other different and obvious aspects, all without departing from the invention. Accordingly, the drawings and descriptions should be regarded as illustrative in nature and not restrictive.

I. Device Overview

Figure 1:
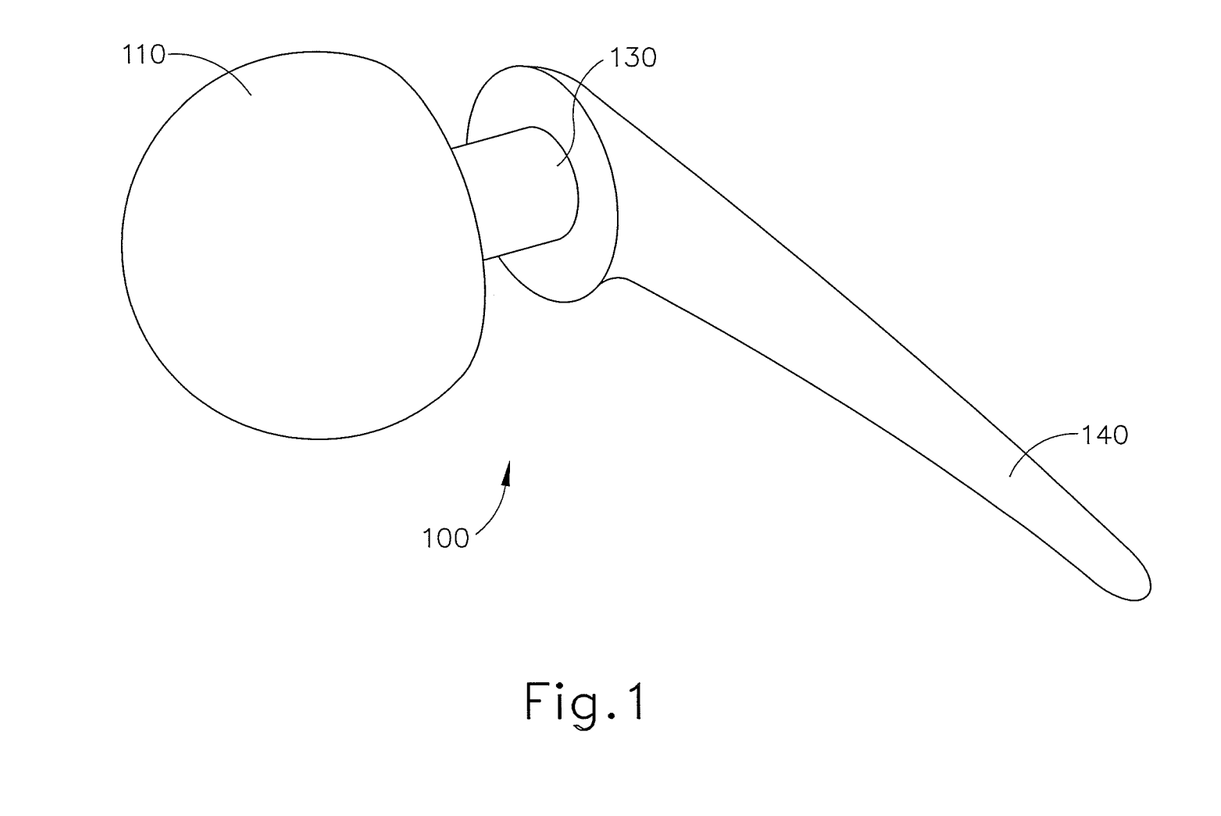
FIG. 1 depicts a perspective view of one embodiment of a shoulder implant device.
Figure 2:
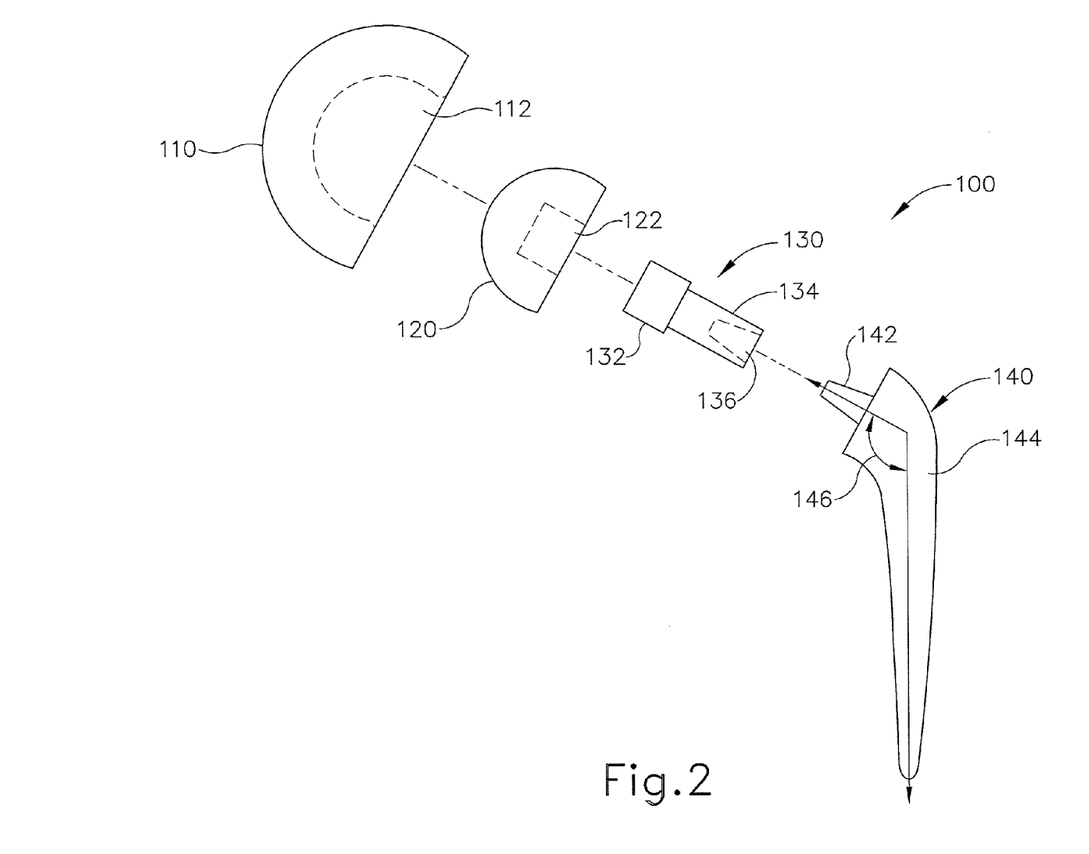
FIG. 2 depicts an exploded side view of one embodiment of the shoulder implant device of FIG. 1.

FIGS. 1-2 show shoulder implant device (100) comprising first head (110), neck (130), and stem (140). Shoulder implant device (100) further comprises second head (120) positioned within first head (110) which can be seen, for example, in FIG. 2. As can be seen from FIGS. 1-2, FIG. 1 depicts a general perspective view of shoulder implant device (100) whereas FIG. 2 depicts an exploded side view of shoulder implant device (100) showing generally how the components of shoulder implant device (100) fit together.

Figure 7:
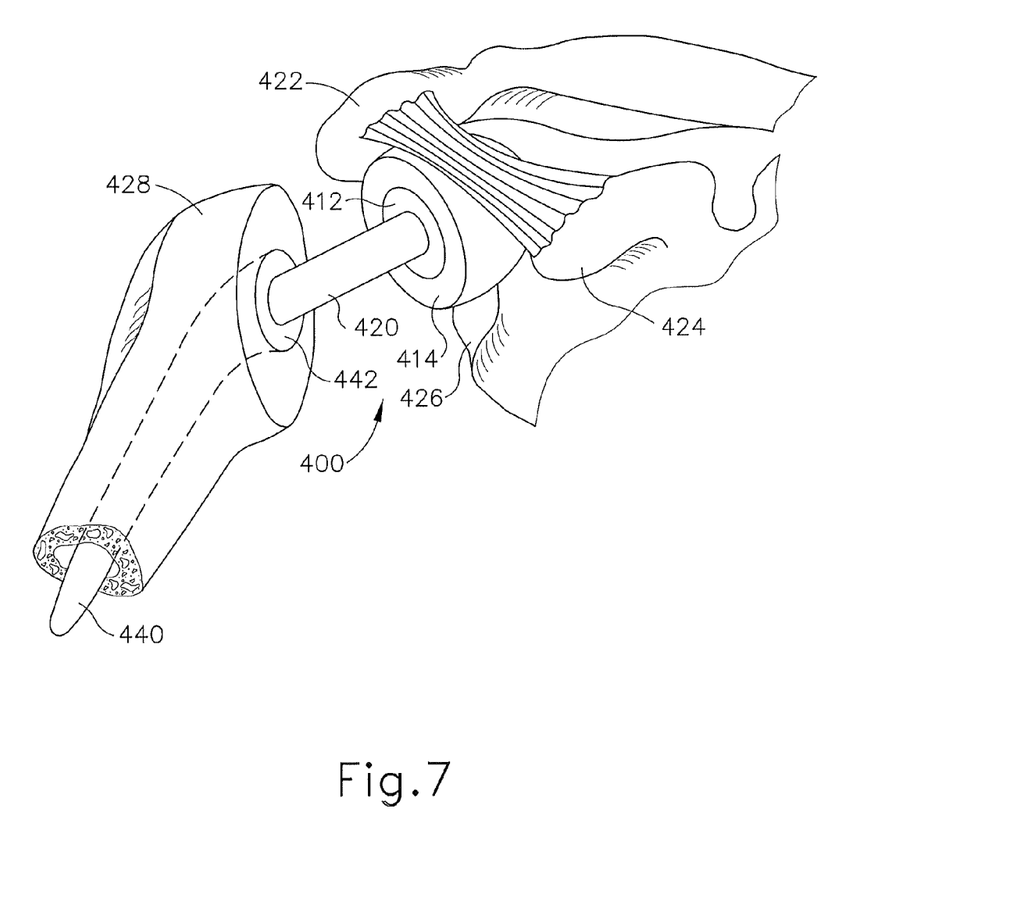
FIG. 7 depicts a front perspective view of an embodiment of the shoulder implant device inserted into the interval defined by the glenoid, the coracoid, and the acromion.

Shoulder implant device (100) is generally implanted into the shoulder portion of a patient. In a merely exemplary shoulder replacement procedure, it will be appreciated that the proximal portion of the humerus will be removed. Thereafter, stem (140) of shoulder implant device (100) will be inserted into a bore within the humerus formed by using, for example, a rasp. Once stem (140) of shoulder implant device (100) is placed into the bore, it will be positioned generally such that first head (110) of shoulder implant device (100) faces towards the body of the patient. In particular, it will be appreciated that the glenoid, coracoid, and acromion form an interval in which first head (110) of shoulder implant device (100) may be placed. To accommodate shoulder implant device (100) it will further be appreciated that the upper portion of the glenoid may be reamed such that the interval defined by the glenoid, coracoid, and acromion better complements first head (110) of shoulder implant device (100). As a result, first head (110) of shoulder implant device (100) may be appropriately seated within the interval created by the reamed upper glenoid, the coracoid, and the acromion. For example, FIG. 7 depicts an embodiment of shoulder implant device positioned within the interval formed by the reamed upper glenoid, the coracoid, and the acromion, which will be discussed in further detail below.

Returning to FIGS. 1-2, first head (110) comprises a hemispherical head. Other suitable head types or shapes may be used as would be apparent to one of ordinary skill in the art in view of the teachings herein. The illustrated embodiment merely demonstrates a hemispherical head. Furthermore, first head (110) comprises a bipolar head such that stem (140) can pivot about first head (110). In some embodiments, first head (110) may comprise a bipolar head such as those made commercially available by Stryker®. However, other hemispherical bipolar heads may be used as would be apparent to one of ordinary skill in the art in view of the teachings herein.

First head (110) further comprises inner articulation portion (112), which is shaped generally to receive second head (120). In the illustrated embodiment, inner articulation portion (112) comprises a hollowed out hemispherical shape such that second head (120) and inner articulation portion (112) mate to form an articulating bearing, which therefore enables the bipolar aspect of first head (110). However, any suitable shape may be used as would be apparent to one of ordinary skill in the art in view of the teachings herein.

First head (110) further comprises an outer diameter of one of the following sizes: 38, 40, 42, 44, 46, 48, 50, and 52 mm. However, any suitable diameter for first head (110) may be used as would apparent to one of ordinary skill in the art in view of the teachings herein. Furthermore, in the exemplary embodiment, inner articulation portion (112) comprises an outer diameter of 22 mm. However, any suitable diameter for inner articulation portion (112) may be used as would be apparent to one of ordinary skill in the art in view of the teachings herein. Indeed, the diameter of inner articulation portion (112) may be selected so as to properly receive second head (112) so as to form an articulating pivot about which neck (130) and subsequently, stem (140) can articulate.

Second head (120), as stated above, is shaped to fit within inner articulation portion (112). Second head (120) and inner articulation portion (112) may engage through use of, for example, a snap retention fitting or a frictional connection. However any suitable connection means may be used as would be apparent to one of ordinary skill in the art in view of the teachings herein. Second head (120) comprises a generally hemispherical exterior, which complements the shape of inner articulation portion (112) as well as allows first head (110) and second head (120) to effectively form a bearing thus allowing smooth motion of second head (120) within first head (110). Thus, when second head (120) engages inner articulation portion (112), second head (120) is able to freely articulate in all directions about the pivot formed by second head (120) and inner articulation portion (112). Second head (120) comprises a neck receiving portion (122), which is shaped to receive neck (130). In some embodiments, neck receiving portion (122) comprises a morse taper having a friction fit to mate with neck (130). In some other embodiments, neck receiving portion (122) may be directly affixed to neck (130) such that second head (120) and neck (130) are integrally formed together. Other suitable means for connecting second head (120) to neck (130) may be used as would be apparent to one of ordinary skill in the art in view of the teachings herein. For example, neck receiving portion (122) may comprise threads, and knob portion (132) of neck (130) may comprise complementary threads, which may enable neck (130) to be screwed into neck receiving portion (122).

Neck (130) comprises knob portion (132), neck body (134), and stem insertion portion (136). Knob portion (132) comprises a generally cylindrical shape and, as mentioned above, is able to engage neck receiving portion (122) in any of the manners mentioned above, including, but not limited to, a morse taper fitting. Neck (130), once connected to second head (120) through knob portion (132), maintains a generally rigid connection between neck (130) and second head (120). However, any suitable type of connection may be used as would be apparent to one of ordinary skill in the art in view of the teachings herein. Neck (130) may comprise any suitable length including, but not limited to 15 mm, 20 mm, 25 mm, 30 mm, 35 mm, and 40 mm. It will be appreciated that any lengths in between may be selected for neck (130) or other suitable lengths longer or shorter than those listed above.

Figure 3:
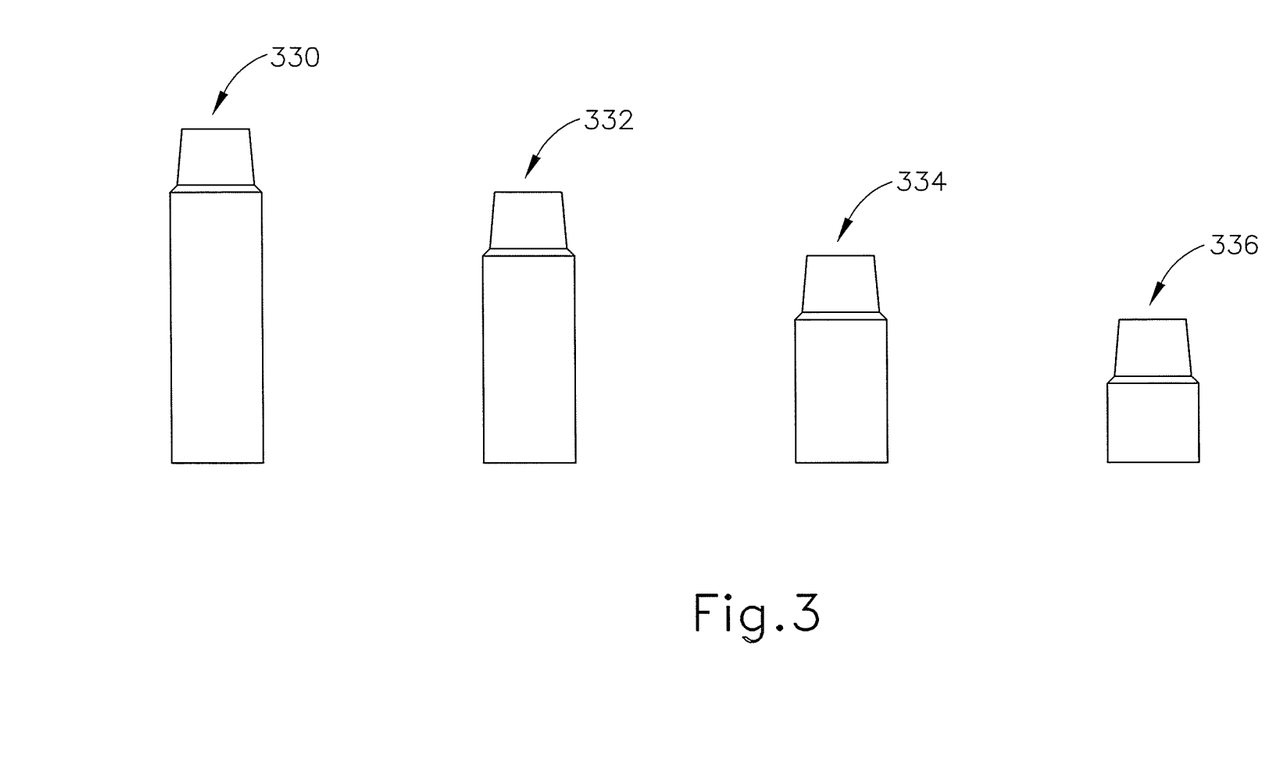
FIG. 3 depicts a side view of a series of neck lengths for use with the shoulder implant device of FIG. 1.

FIG. 3 shows a variety of necks (330, 332, 334, 336), which may be used with shoulder implant device (100) shown in FIGS. 1-2. Necks (330, 332, 334, 336) may comprise a wide range of sizes that may be selected for use with shoulder implant device (100) based on several factors. For example, the individual anatomy of the patient may influence the length of neck (330, 332, 334, 336) used. In the case that the patient is large boned with a larger shoulder region, a longer neck (330, 332, 334, 336) may be required. In other cases, if the patient is small boned, then a shorter neck (330, 332, 334, 336) may be required. Furthermore, the length of neck (330, 332, 334, 336) may also be selected based on the seating of first head (110) (e.g., of FIG. 1) within the interval formed by the coracoid, the acromion, and the reamed upper glenoid. For example, it will be appreciated that due to the reaming of the upper glenoid, which will be described in further detail below, first head (110) may be seated more deeply within the coracoid, the acromion, and the glenoid interval. As a result, for first head (110) to properly seat against the upper glenoid, a longer neck (330, 332, 334, 336) may be selected than might be used in a typical shoulder replacement procedure for implanting a typical shoulder replacement. Appropriate selection of the length of neck (330, 332, 334, 336) will be apparent to one of ordinary skill in the art in view of the teachings herein.

It will further be appreciated that necks (330, 332, 334, 336) are representative examples of different possible lengths for neck (130) depicted in FIGS. 1-2. However, the length for neck (130) depicted in FIGS. 1-2 need not be limited to the lengths represented by necks (330, 332, 334, 336) in FIG. 3 which are merely exemplary. Neck lengths may range from 6 mm to 40 mm depending on the shoulder anatomy of the patient. In some exemplary procedures, a surgeon could insert trial necks of different lengths to determine the appropriate neck length before deciding on a particular neck length for the patient.

Furthermore, in the illustrated embodiment, neck (130) comprises a gradual taper from one end of neck (130) to the opposing end of neck (130). In other embodiments, neck (130) may comprise a consistent width throughout the length of neck (130). Indeed, in looking at FIG. 3, necks (330, 332, 334, 336) comprise a generally cylindrical shape having a slightly tapered end. It will be appreciated that shape of necks (330, 332, 334, 336) may be such that necks (330, 332, 334, 336) are readily compatible with commercially available stems and bipolar heads. Of course, any suitable shape for neck may be used as would be apparent to one of ordinary skill in the art in view of the teachings herein.

Returning to FIGS. 1-2, stem insertion portion (136) may be shaped to mate with mating portion (142) of stem (140). Mating portion (142) may comprise, for example, a morse taper. However, any suitable connection means between stem insertion portion (136) and mating portion (142) may be used as would be apparent to one of ordinary skill in the art in view of the teachings herein. For example, rather than a morse taper, a threaded portion of stem insertion portion (136) may be used to screw in a portion of mating portion (142), or a snap fitting between stem insertion portion (136) and mating portion (142) may be used.

Stem (140) further comprises shaft (144). Shaft (144) is constructed to be implanted into the humerus of a patient once the proximal portion of the humerus is removed and an opening in the humerus is made using, for example, a rasp, to accommodate stem (140). In some embodiments, stem (140) may comprise a "Solar" stem by Stryker® or a similarly styled stem from DePuy®. Furthermore, stem (140) and mating portion (142) define stem angle (146). Stem (140) and mating portion (142) may be constructed such that stem angle (146) comprises an angle of approximately 125°. In other embodiments, stem angle (146) may comprise an angle of greater than 125°. In some embodiments, an angle of 140° may be selected for stem angle (146). It will be appreciated that rather than a single angle, different angles for stem angle (146) may be the appropriate angle depending on the anatomy of the patient as well as the placement of shoulder implant device (100) within the patient.

The various pieces and components of shoulder implant device (100) may be constructed, for example, of stainless steel, titanium, ceramic, any other suitable material, or any combination thereof as would be apparent to one of ordinary skill in the art in view of the teachings herein.

Figure 4:
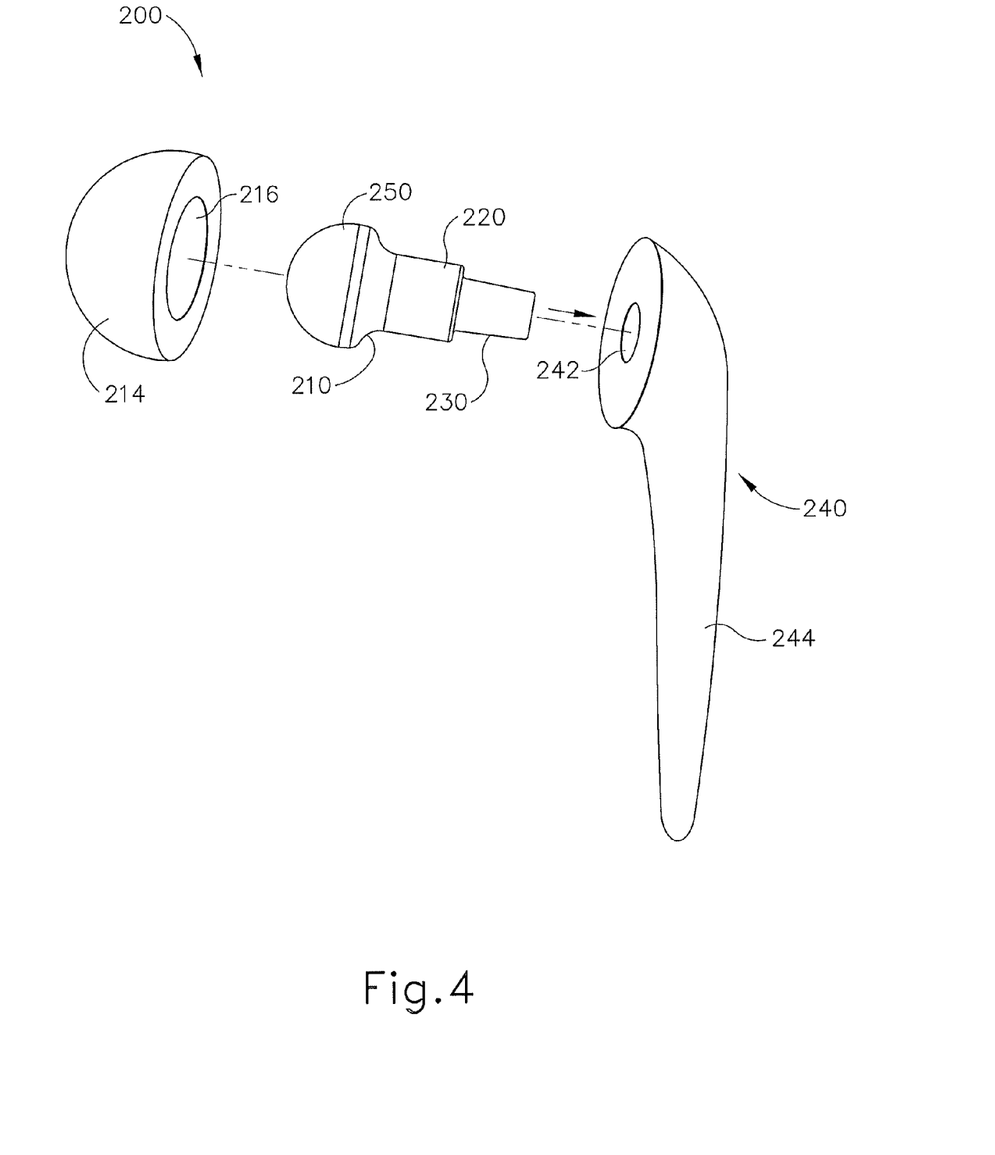
FIG. 4 depicts an exploded side view of an alternative embodiment of a shoulder implant device.
Figures 5, 6:
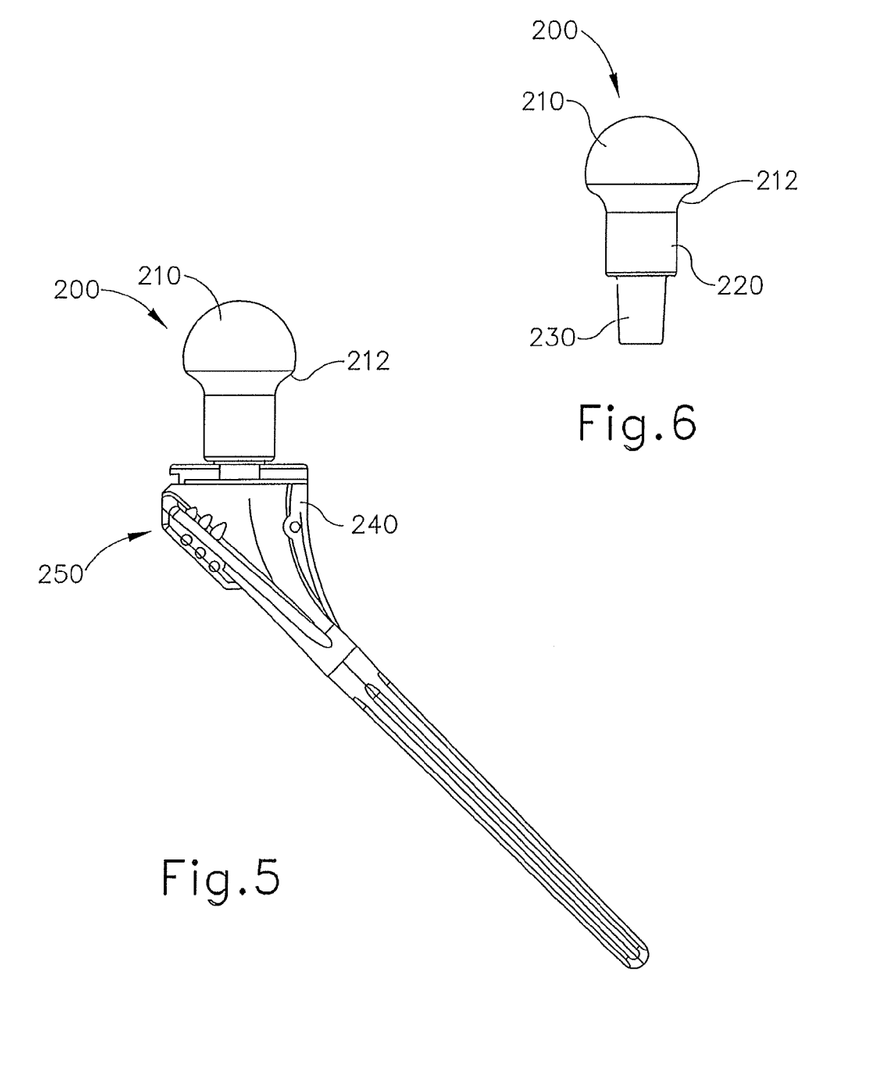
FIG. 5 depicts a side view of a stem and an adapter of the shoulder implant device of FIG. 4.
FIG. 6 depicts a side view of the adapter of FIG. 5.

FIGS. 4-6 show an alternative embodiment of shoulder implant device (200) having adapter (250). Adapter (250) may be used to directly connect stem (240) with bipolar head (214). Adapter (200) may be used instead of the second head (120) and neck (130) construction as shown in FIGS. 1-2.

Adapter (250) comprises spherical portion (210) connected to cylindrical body (220) through moderate slope (212). Cylindrical body (220) then connects to tapered mating portion (230). Spherical portion (210) of adapter (250) may sized so as to fit within inner articulation portion (216) of bipolar head (214) such that adapter (250) and bipolar head (214) form a ball joint when spherical portion (210) is inserted into inner articulation portion (216) of bipolar head (214).

Cylindrical body (220) comprises a length of approximately 10 mm, as can be seen, for example, in FIG. 5; however, any suitable length for cylindrical body (220) may be used as would be apparent to one of ordinary skill in the art in view of the teachings herein. It will be appreciated that the length of cylindrical body (220) may be selected in a substantially similar way as selecting the length of neck (130, 330, 332, 334, 336) in FIGS. 1-3. In other words, cylindrical body (220) may need to be longer, than, for example, a neck of a typical shoulder implant device due to reaming of the upper glenoid, which will enable bipolar head (214) to be seated more deeply into the interval formed by the coracoid, the acromion, and the reamed upper glenoid.

Furthermore, bipolar head (220) may have an outer diameter of, for example 50 mm. However, any suitable diameter of bipolar head (220) may be used as would be apparent to one of ordinary skill in the art. As an example, any of the sizes for the bipolar head shown in FIGS. 1-2, which include diameters, for example, between approximately 38 mm and 52 mm, may be selected for bipolar head (220). Other suitable sizes will be apparent to one of ordinary skill in the art in view of the teachings herein.

Tapered mating portion (230) then connects to mating portion (242) of stem (240). It will be appreciated that stem (240) also comprises a shaft (244), which may be constructed in a substantially similar manner as shaft (144) shown, for example, in FIGS. 1-2. Furthermore, it will be appreciated that adapter (250) may be constructed and fitted specifically to adapt to commercially available stems and bipolar heads with the exception that cylindrical body (220) may comprise a longer length than might otherwise be used with a commercially available stem and bipolar head as is described above.

II. Procedure Overview

Generally speaking, shoulder implant device (100, 200) shown in FIG. 1, 2, or 4 may be used in a shoulder replacement procedure. Such an exemplary procedure is also outlined in FIG. 10. It will be appreciated that other suitable uses for shoulder implant device (100, 200) may be used as would be apparent to one of ordinary skill in the art in view of the teachings herein. It will further be appreciated that shoulder implant device (100, 200) may generally be used in a procedure with a patient having a generally functioning deltoid muscle. It is understood that the deltoid muscle need not necessarily be in perfect working condition. So long as the patient's deltoid muscle function is not materially compromised, the procedure described below may be used with shoulder implant device (100, 200).

FIG. 7 shows shoulder implant device (400) inserted into the interval formed by a reamed upper glenoid (426), coracoid (424), and acromion (422) within a target shoulder area. It will be appreciated that glenoid (426), coracoid (424), and acromion (422) form an interval in which shoulder implant device (400) may be inserted. However, to seat shoulder implant device (400) more deeply into the interval, the upper portion of glenoid (426) should be reamed. It will be appreciated that shoulder implant device (400) of FIG. 7 may be constructed substantially similar to the teachings of shoulder implant device (100, 200) shown in FIG. 1, 2, or 4. Shoulder implant device (400), comprises bipolar head (414), neck (420) inserted into inner articulation portion (412) of bipolar head (414), and stem (440). Ultimately, stem (440) may be inserted into bore (442) of humerus (428) to secure stem (440), while bipolar head (414) is positioned within the interval formed by reamed upper glenoid (426), coracoid (424), and acromion (422).

Figure 10:
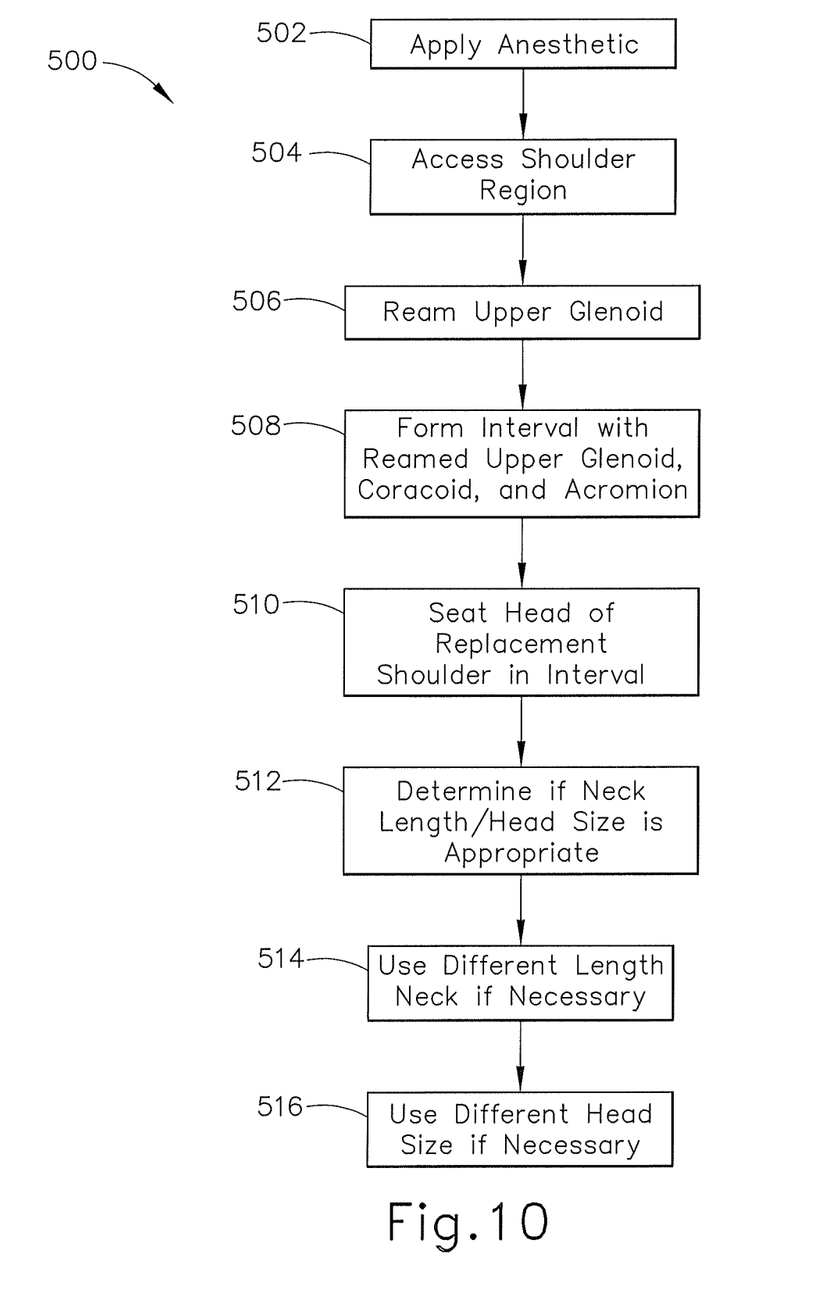
FIG. 10 depicts a flowchart view of an exemplary procedure for use with the shoulder implant device.

In one merely exemplary procedure, a patient may be provided with an anesthetic, for example, a general anesthetic, such as shown in step (502) of FIG. 10. Patient may then be placed in a slightly head up position. However, any suitable position for patient may be used.

Next, the shoulder region of the patient may be accessed as shown in step (504) of FIG. 10. In preparation for an incision to access the region, the target arm and shoulder may be prepared with, for example, Betadine soap and/or betadine solution. Furthermore, the target arm or shoulder may be painted with a Betadine solution or any other suitable topical antiseptic. Any suitable antiseptic may be used as would be apparent to one of ordinary skill in the art in view of the teachings herein. The area for incision may be draped in an appropriate free sterile fashion. Furthermore, preoperative antibiotics, for example cephalosporin may be administered intravenously. Other variations to this preparation process will be apparent to one of ordinary skill in the art in view of the teachings herein.

A deltopectoral incision may be made to access the relevant shoulder site on the patient and thereby aiding in forming the deltopectoral interval in which the cephalic vein remains protected. In some embodiments of the procedure, if the subscapularis tendon is present, it may be taken down and tagged from the lesser tuberosity. In other embodiments of the procedure, if the subscapularis tendon is present, it may be taken down in a Z-Plasty fashion, if it is to be lengthened upon repair. The user should be careful to make sure the cephalic vein is not injured in the process. The subscapularis tendon may be taken from the Lesser Tuberosity or alternatively may then be opened using a Z-plasty incision and then tagging both ends. The subscapularis tendon may be tagged with a suture. Any abnormal tissue in the shoulder joint may be removed. In some exemplary embodiments, for example, a rongeur may be used to remove any abnormal tissue.

The shoulder may then be dislocated anteriorly. Other suitable ways of dislocating shoulder may be used as would be apparent to one of ordinary skill in the art in view of the teachings herein. In the event that further abnormal tissue is discovered, it may be removed. During the procedure, the shoulder may be irrigated using, for example, a saline solution. However other methods of irrigation may be suitable as would be apparent to one of ordinary skill in view of the teachings herein. Humeral head of humerus (428) is removed to make room for shoulder implant device (400). Humeral Head may be resected at approximately 45 degrees of retroversion at an angle of approximately 130 degrees. Other suitable angles may be used as would be apparent to one of ordinary skill in the art in view of the teachings herein. Once the humeral head is removed, it may be discarded. Furthermore, bore (442) is reamed in humerus (428) using, for example, a rasp, to accommodate stem (440). Bore (442) may be reamed at an angle of approximately 45 degrees of retroversion, but any suitable angle may be used as would be apparent to one of ordinary skill in the art in view of the teachings herein. Stem (440) may be secured within bore (442) using a cement or alternatively may be secured due to its frictional fitting.

Figure 8:
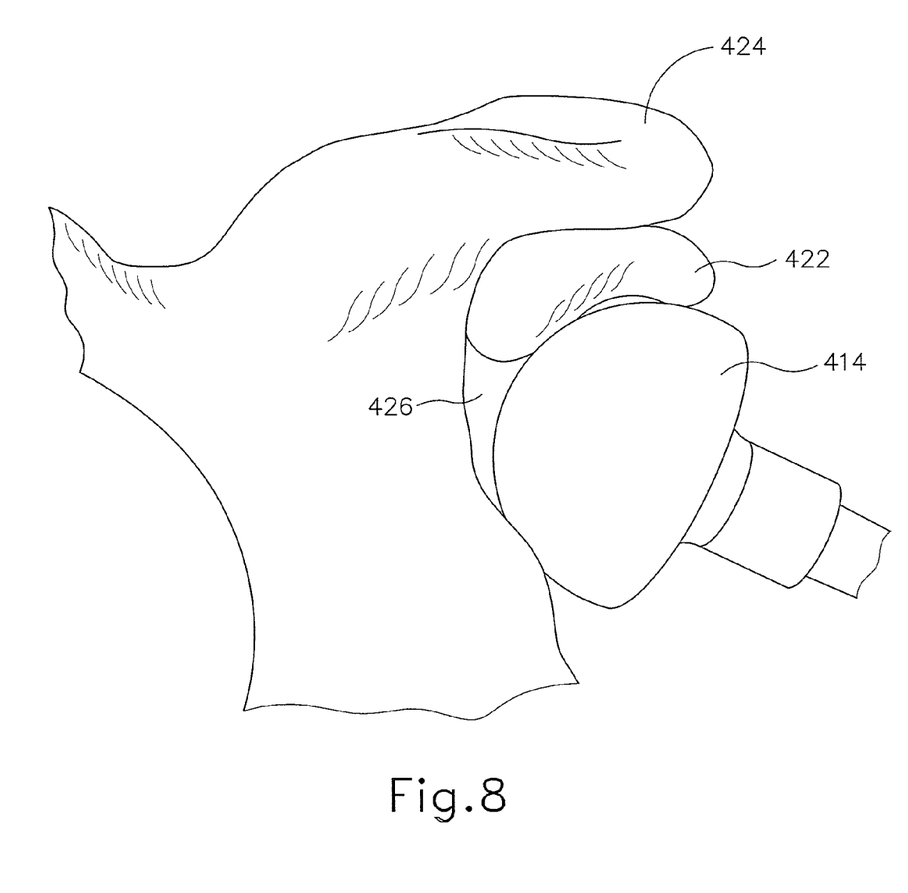
FIG. 8 depicts a close-up, perspective view of the upper glenoid highlighting the portion of the upper glenoid to be reamed shown with a typical shoulder implant device.

Also during the procedure, the upper of glenoid (426) is reamed as recited in step (506) of FIG. 10. It will be appreciated that reaming of glenoid (426) will likely not be uniform across all patients, especially considering that individual patients' anatomy may differ. For example, if subscapularis is not present during the procedure within the particular patient, then the user may attempt to preserve at least a portion of the anterior superior glenoid, thereby somewhat enhancing bipolar stability. FIG. 8 highlights an exemplary target portion of glenoid (426) for reaming. Reaming of glenoid (426) may be accomplished by, for example, using a spherical reamer, an acetabular reamer, a burr reamer, or any other suitable reaming device as would be apparent to one of the ordinary skill in the art in view of the teachings herein. The reaming may begin with a small reamer removing only the upper margin of glenoid (426) starting to create a concave cavity bordered by the base of coracoid (424), acromion (422) and the lower half of glenoid (426). It may be gradually enlarged by using a slightly larger acetabular, similarly suitable, reamer to create a cavity that will accept bipolar head (414), thereby forming an appropriate interval as shown in step (508) of FIG. 10. Furthermore, to determine the appropriate degree of reaming as well as the overall shape of the reaming, several factors should be balanced.

First, the reaming of glenoid (426) should be performed so as to provide upward support of bipolar head (414), and the curvature of reaming should be such that bipolar head (414) will further avoid slipping. In other words, the user must essentially keep intact enough of the lower portion glenoid (416) with a suitable curvature in order to create a sufficient lip to support bipolar head (414). Bipolar head (414) may be selected to be approximately 1-2 millimeters larger than the cavity created, but other suitable sizes for bipolar head (414) may be used as would be apparent to one of ordinary skill in the art in view of the teachings herein.

Second, it will be appreciated in many patients undergoing this procedure that the subscapularis is damaged, which generally functions to provide anterior stability for the shoulder joint. By reaming the upper portion of glenoid (426) sufficiently deep, once bipolar head (414) is placed against glenoid (426), coracoid (424) will provide anterior stability for the shoulder. It will further be appreciated that under typical circumstances, bipolar head (414) does not necessarily come in contact with coracoid (424). However, in the event that bipolar head (414) slides anteriorly, bipolar head (414) will in fact contact coracoid (424), which will prevent further anterior displacement.

Third, it will be appreciated that reaming of glenoid (426) may be performed so that the shape of glenoid (426) after reaming approximately matches or complements the shape of bipolar head (414), which will be seated against glenoid (426).

Finally, it will be appreciated that as more glenoid (426) is reamed, shoulder implant device (400) may provide a greater mechanical advantage for the deltoid for motion of the arm of the patient due to the length of the fulcrum for the deltoid increasing. Thus, a deeper reaming of glenoid (426) may be desirable.

Figure 9:
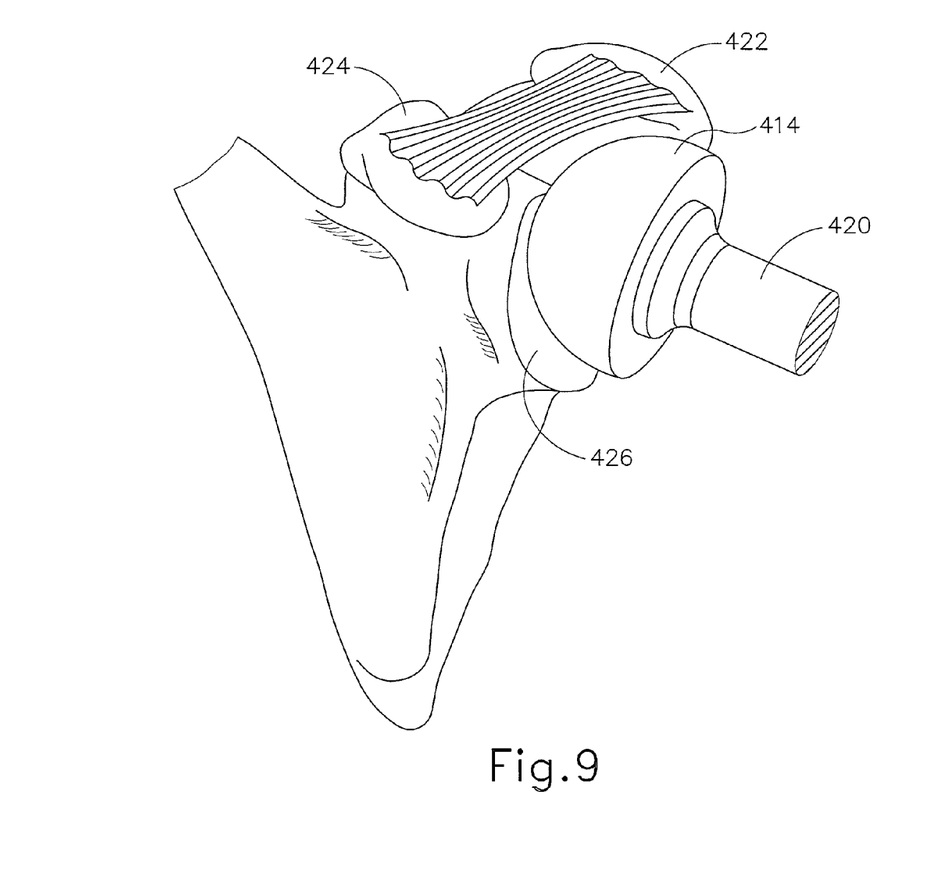
FIG. 9 depicts a close-up, perspective view of the upper glenoid after being reamed and an embodiment of the shoulder implant device being placed into the interval defined by the glenoid, the coracoid, and the acromion.

However, in reaming glenoid (426) in light of these considerations, it will further be appreciated that reaming of glenoid (426) may be limited in some circumstances as a result of the overall width and associated stability of glenoid (426) as more glenoid (426) is reamed. Furthermore, it will be appreciated that too much reaming of glenoid (426) may lead to undesirable effects regarding the structural integrity of coracoid (424) as coracoid (424) may be subject to further stress. As a result, though individual anatomy may differ, it will be appreciated that the above considerations provide sufficient guidance for one of ordinary skill in the art to sufficiently ream glenoid (426) to appropriately seat shoulder implant device (400). Thereafter, shoulder implant device (400) may be implanted by securing stem (440) into bore (442) and bipolar head (414) against reamed glenoid (426) as can be seen in FIG. 9.

Thus, during the procedure, shoulder implant device (400) may be impacted with bipolar head (414) for seating within the interval of the glenoid (426), coracoid (424), and acromion (422) as in step (510) of FIG. 10. Or bipolar head (414) may be impacted after the initial incision is made. Furthermore, in some embodiments, a trial bipolar head (414) may first be used to determine whether the size of bipolar head (414) is appropriate followed by removal of the trial head and addition of the permanent head. It will be appreciated that, as shown in step (512), a different length for neck (420) or a different size for bipolar head (414) may be required. Thus, the user or physician may wish to attempt using a variety of lengths for neck (420) or sizes for bipolar head (414). It will be appreciated that an appropriate length for neck (420) must be selected. In one embodiment of the procedure, the user could attempt to fit several different lengths for neck (420) until one is decided upon as shown in step (514) of FIG. 10. Furthermore, different shapes and/or radii of bipolar head (414) may need to be tested to determine to decide on an appropriate bipolar head (414) as shown in step (516) of FIG. 10.

Once shoulder implant device (400) is implanted, the shoulder may be once again reduced. It will be appreciated that the shoulder may be reduced and the range of motion of shoulder may be tested to verify that the proper size of bipolar head (414) and neck (420) is selected as described above. In the event that test and/or temporary components are tested, such as a test bipolar head (414) or neck (420), the user may then replace the test components with permanent components to be used and reduce the shoulder of the patient. Furthermore, to the extent that any subscapularis tendon requires repairing, it may be repaired in a lengthened fashion by using, for example, Ethibond® brand interrupted figure-eight suture. However, other suitable suture tools may be used as would be apparent to one of ordinary skill in the art in view of the teachings herein. Furthermore, the deltopectoral incision may then be closed by repairing it with, for example, suture. However, other methods of repairing the deltopectoral incision may be used as would be apparent to one of ordinary skill in the art in view of the teachings herein.

Subcutaneous tissue may be then reapproximated over Hemovac drains with a combination of interrupted buried suture. The interrupted buried suture may comprise, for example, a 0 Vicryl and/or a 2-0 Vicryl interrupted buried suture. If necessary, the skin may also be reapproximated with skin staples. The wound may also be dressed to aid in rehabilitation of the wound and for patient recovery. The arm of the patient may be placed into, for example, a shoulder immobilizer or sling.

Having shown and described various embodiments in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, embodiments discussed above are illustrative and are not required. Accordingly, the scope of the present invention should not be limited to the details of structure and operation shown and described in the specification and drawings.

I claim:

1. A method of replacing a shoulder of a patient with an implantable device, the implantable device comprising a bipolar head, neck, and stem, the method comprising:
    (a) accessing a first interval formed by the upper glenoid, the coracoid, and the acromion of the patient;
    (b) reaming at least a portion of the upper glenoid;
    (c) forming a second interval with the reamed upper glenoid, the coracoid, and the acromion, wherein the second interval is recessed more deeply into the shoulder region of the patient than the first interval; and
    (d) seating the bipolar head within the second interval.

2. The method of claim 1, further comprising determining whether the bipolar head is seated sufficiently deep within the second interval.

3. The method of claim 1, further comprising trialing different neck lengths.

4. The method of claim 1, further comprising removing a portion of the humerus and inserting the stem into the humerus.

5. The method of claim 1, further comprising selecting a neck length between 5 mm and 60 mm.

6. A method of replacing a shoulder joint of a patient using an implantable device, the method comprising:
    (a) surgically accessing a shoulder joint;
    (b) removing at least a portion of the humerus;
    (c) removing at least a portion of the upper glenoid;
    (d) forming an interval with the upper glenoid, the coracoid, and the acromion;
    (e) inserting the implantable device into the interval such that at least a portion of the implantable device is in communication with the upper glenoid;
    wherein the shoulder joint has rotator cuff arthropathy.

7. The method of claim 6, wherein the implantable device comprises a stem, head, and neck.

8. The method of claim 6, further comprising trialing different lengths of the implantable device.

9. The method of claim 6, wherein the act of removing the upper glenoid is performed by reaming the upper glenoid.

10. The method of claim 6, further comprising inserting a test implantable device prior to the step of inserting the implantable device.

* * * * *